United States Patent [19]

Poor et al.

[11] Patent Number: 5,211,820
[45] Date of Patent: May 18, 1993

[54] GAS ANALYSIS SYSTEM FOR FURNACES AND THE LIKE

[75] Inventors: Ralph P. Poor; Michael J. Huber, both of Toledo; Garry W. Barbee, Waterville, all of Ohio

[73] Assignee: Surface Combustion, Inc., Maumee, Ohio

[21] Appl. No.: 862,998

[22] Filed: Apr. 6, 1992

Related U.S. Application Data

[62] Division of Ser. No. 680,298, Apr. 4, 1991, Pat. No. 5,137,616.

[51] Int. Cl.$^5$ ............................................ G01M 27/26
[52] U.S. Cl. ............................ 204/153.18; 204/424; 204/426; 204/427; 432/23
[58] Field of Search ...................... 432/2, 18, 23, 41; 204/153.18, 424, 425, 426, 427, 428, 429

[56] References Cited

U.S. PATENT DOCUMENTS

| | | | |
|---|---|---|---|
| 4,101,404 | 7/1978 | Blumenthal et al. | 204/428 |
| 4,147,513 | 4/1979 | Bienkowski et al. | 23/232 |
| 4,178,358 | 12/1979 | Smith et al. | 432/2 |
| 4,249,965 | 2/1981 | Schultz | 148/27 |
| 4,310,302 | 1/1982 | Thekdi et al. | 432/205 |
| 4,485,002 | 11/1984 | Wunning | 204/428 |
| 4,490,108 | 12/1984 | Petzi | 432/23 |
| 4,588,493 | 5/1986 | Blumenthal et al. | 204/410 |
| 4,592,825 | 6/1986 | Crevoiserat | 204/428 |
| 4,596,526 | 6/1986 | Soliman | 432/23 |
| 4,606,807 | 8/1986 | Mendenhall | 204/433 |
| 4,759,827 | 7/1988 | Okada et al. | 204/153.18 |
| 4,784,728 | 11/1988 | Capone | 204/1 T |
| 4,805,881 | 2/1989 | Schultz et al. | 266/257 |
| 4,808,294 | 2/1989 | Beuret et al. | 204/428 |
| 4,875,981 | 10/1989 | Usami et al. | 204/406 |
| 4,875,990 | 10/1989 | Kudachi et al. | 204/428 |
| 5,074,987 | 12/1991 | Thompson | 204/153.18 |

OTHER PUBLICATIONS

Operating Instructions (Not Dated) For O$_2$ Systems, Inc. S-1050 Sensor Assembly.
Autolite Spec. Sheet–Heated Titania Oxygen Sensor Probe.
Allied Automotive Drawing 3235862 Dated Apr. 10, 1985.
Allied Automotive Drawing 3235796 Dated Mar. 16, 1983.

*Primary Examiner*—John Niebling
*Assistant Examiner*—Bruce F. Bell
*Attorney, Agent, or Firm*—Body, Vickers & Daniels

[57] ABSTRACT

A system for use in sensing the oxygen content of an industrial furnace gas typically containing hydrocarbons or hydrogen is disclosed. The system utilizes a conventional automotive EGR oxygen sensor probe positioned in an especially configured housing employing downstream flow regulating means in combination with an orificing plate in the housing to provide uniform distribution of the endothermic gas at a low temperature about the sensor to insure accurate sensor readings with minimal carbon deposition. The electrical contacts at the oxygen sensor's inner and outer electrolyte surfaces are periodically switched to an electrical power supply to cause current to flow through and heat the electrolyte to elevated temperatures while air is flowed over the electrolyte's surfaces to achieve burn out of any carbon deposits and restore the life of the oxygen sensor probe. In addition, a portion of the sensor is thermally shielded to maintain somewhat equal reference air and furnace gas temperatures to produce consistent and reliable output signals from the oxygen sensor probe.

2 Claims, 6 Drawing Sheets

GAS ANALYSIS SYSTEM FOR FURNACES AND THE LIKE

This application is a divisional of Ser. No. 680,298, filed Apr. 4, 1991, which became U.S. Pat. No. 5,137,616 on Aug. 11, 1992.

This invention relates generally to oxygen sensing probes and, more particularly, to a system or arrangement for determining gas composition which uses a conventional oxygen sensing probe to produce improved results.

The invention is particularly applicable to and will be described with specific reference to an oxygen sensing arrangement employed in the industrial furnace art. The invention, however, has broader application outside the furnace art and is particularly suited to sense composition of any gas stream containing hydrocarbons. As an example, the invention could be used to analyze automotive exhaust emissions.

INCORPORATION BY REFERENCE

U.S. Pat. No. 4,606,807 to Mendenhall dated Aug. 19, 1986 is incorporated herein by reference and made a part hereof so that conventional concepts, principles and equipment used in the art need not be explained in significant detail in the specifications hereto. Also incorporated by reference herein for the same purposes are Schultz U.S. Pat. No. 4,805,881; Schultz U.S. Pat. No. 4,249,965; Bienkowski U.S. Pat. No. 4,147,513; Capone U.S. Pat. No. 4,784,728 and Blumenthal 4,588,493.

BACKGROUND OF THE INVENTION

Oxygen sensing probes are well known conventional instruments which sense the oxygen content of a gas. In the industrial furnace field, the oxygen is correlated by known formula to $CO_2$ or dew point (water vapor) composition of the gas which is used to control the furnace atmosphere and thus the heat treat process. In the industrial heat treat art, the oxygen sensing probe is usually of the type which has a solid electrolyte which is in contact on one side with a reference gas (air) and on its opposite side with the furnace atmosphere whose oxygen content is to be measured. When the electrolyte is stabilized zirconia, an Emf is generated between the sides of the electrolyte. The magnitude of the voltage generated from the ion activity of the electrolyte is dependent upon the temperature of the electrolyte and the log of the ratio of the oxygen partial pressure on the opposing sides of the electrolyte. Another type of oxygen sensor, used in the automotive field, is one wherein the electrical resistance of the sensor, i.e. titania, changes with the amount of the oxygen present in the gas. The present invention is directed in its preferred embodiment to the oxygen sensing probe which uses a stabilized zirconia electrolyte although the invention is believed applicable to a titania sensor.

It is well known in the industrial furnace art to use oxygen sensing probes to control the furnace atmosphere. The probes are conventionally used for atmospheres ranging anywhere from neutral (i.e. typically used in furnace annealing heat treat processes) to rich or reducing or endothermic (i.e. typically used in carburizing heat treat furnaces). However, there is theoretically no reason why the oxygen sensing probe cannot be used to sense lean or oxygen enriched furnace atmospheres so long as the oxygen content in the furnace atmosphere is less than the oxygen content present in air.

When the oxygen sensing probes are used in a rich or reducing furnace atmosphere heavy in hydrocarbon concentration (such as carburizing processes which require the carbon potential in the atmosphere to be closely controlled), carbon deposits accumulate on the probe and in time adversely affect the probe's reading. The life of the probe in such applications is significantly reduced. The same problem, short life, is encountered in endothermic gas generators which generate rich, reducing gases typically supplied to carburizing furnaces.

A. GAS GENERATOR PRIOR ART

In the heat treat art and particularly for carburizing heat treat process, an endothermic gas is supplied to the heat treat furnace. This gas, which has a specific composition as defined hereafter, disassociates at elevated temperatures to produce elemental carbon which is infused into the case of the workpiece. The endothermic gas can be generated within the furnace from an internal gas generator such as shown in Schultz et al U.S. Pat. No. 4,805,881 or, alternatively, the gas can be generated by controlling and firing the burner's products of combustion directly into the furnace and injecting additional quantities of an elemental gas such as hydrogen to create a furnace atmosphere with carburizing potential. However, the system which is in widest use generates the endothermic gas from an external gas generator situated remote from a bank of heat treat furnaces and the gas is piped from the generator to the furnaces. Basically, there are two types of endothermic external gas generators in use. One type reacts methanol with nitrogen in the presence of heat to produce an endothermic carrier gas. The other, more common, external gas generator reacts natural gas with air over a catalyst bed to produce the endothermic gas. No matter which external generator is used, the system requires that the generator's output be varied because the heat treat process cycles vary the amount of gas needed during each cycle and the furnaces are, at any given time, at different points in different heat treat cycles. Because the quality of the endothermic gas produced is a time-temperature function, some mechanism for sensing the gas composition from the gas generator has to be used to control the gas generator process.

The control mechanism used for controlling the gas generator takes the form of an oxygen sensing device which senses the presence of oxygen, or more precisely, the absence of oxygen so that an appropriate controller can adjust the output of the gas generator. Prior to the present invention, the gas generator oxygen sensor in the heat treat art had progressed to the device disclosed in Mendenhall U.S. Pat. No. 4,606,807. The '807 patent discloses a conventional, zirconium oxide sensor used in the automotive EGR (exhaust gas recirculation) system to control pollution emissions from an internal combustion engine. Because the automotive oxygen sensor is inexpensive and easily removed from the "hot box" to which it is attached in the event of failure to reduce down time of the system, the unit disclosed in the '807 patent has resulted in wide scale commercial acceptance for external, endothermic gas generators within the heat treat art. However, in order to measure the oxygen potential of the endothermic gas with the automotive sensor, the '807 patent had to heat the endothermic gas by means of an external heater surrounding the automotive sensor to high temperatures and preferably temperatures at the range of about 1400° F. and higher to obtain consistent electrical readings from the automotive probe. At this temperature, carbon deposition occurs at the tip of the oxygen sensor eventually fouling the sensor and producing inaccurate readings. In many instances, a life as short as two weeks has been experienced. When the oxygen sensing probe fails, the system has to shut down to not only permit replacement of the probe, but also so that the carbon in the hot box can be burned out. In fact, the assignee of the present invention has encountered such severe life problems that heaters and special chambers downstream of the sensor tip have had to be employed to force carbon deposition to occur away from the oxygen sensor to extend sensor life. Even with this "fix", the extended life of the sensor is just barely acceptable from a system down time consideration and burnout requiring that the system go down is still required.

Another significant problem afflicting the design shown in the '807 patent results from gas "flare" which is the term used to describe the gas exiting the "hot box" after it is sensed by the oxygen sensor. Because of the small volume of the gas sample which is measured by the oxygen probe, the gas is simply vented into ambient air about the "hot box". Since the gas is at an elevated temperature, a slight flame or "flare" occurs at the point where the sampled gas meets ambient air (producing a combustible mixture) and ignites. Depending upon drafts present in the ambient air or variation in pressure from the tap from the main endothermic gas line, air can and does infiltrate into the "hot box" causing erroneous signals. The problem has been severe especially when it is recognized that the oxygen content of the endothermic gas which is being sensed is in the range of parts per million.

Further, a less readily apparent problem with the '807 device relates to the turndown ratio that the system can achieve which in turn is directly correlated to the range over which the sensor is accurate. That is, as the carburizing process proceeds in the heat treat furnaces, the burners are turned down in their heat output range to maintain a desired temperature and the flow of the carrier gas is similarly cut back so that the "make up" carrier gas supplied balances the carbon absorbed into the case of the workpieces being heat treated. This in turn means the output of the gas generator must be turned down and that range is typically sized today at 2 or at best 3:1. Obviously, the cost to operate the generator can be enhanced if the turndown ratio can be improved. However, as the generator flow is turned down, the pressure in the tap line to the '807 sensor varies limiting the generator turn down ratio to the noted ranges for the sensor shown in the '807 patent.

B. FURNACE PROBE PRIOR ART

Unlike the gas generator oxygen probe which utilizes an automotive EGR oxygen sensor, furnace probes in use today are especially constructed zirconium electrolyte cells which are constructed to be mounted to and extend through the furnace casing. Because the furnace oxygen sensing probe is within the furnace, it is heated to the furnace temperature, and thus furnace probes do not need nor have any mechanism for heating the electrolyte which is required in a gas generator arrangement. On the other hand, because some furnaces do not develop significant pressure, the electrolyte in the furnace probe must be shaped in a long length fashion with an appropriate sheath which can "catch" a sufficient "flow" of furnace atmosphere to produce accurate readings. An example of such arrangement is disclosed in Blumenthal 4,588,493. Furnace oxygen sensing probes having long length electrolytes inherently have sealing problems because the internal side of the electrolyte in contact with ambient air must be likewise lengthened. Further, there is a problem also resulting from the varying temperature differential between hot furnace atmosphere and ambient air temperature which can vary along the long electrolyte length. Such problems adversely affect the accuracy of the probe. However, the major problem effecting furnace probes is the carbon deposition which is the same problem afflicting the gas generator probe. It must be noted that the carburizing process requires that the temperature of the furnace atmosphere and the gas composition of the furnace atmosphere is established at a value whereat elemental carbon is precipitated. By placing the oxygen probe into the furnace, the carbon being produced in the furnace must eventually be deposited on the outer, electrolyte surface of the oxygen sensing probe.

Attempts to rectify this problem have included "burnout". In the furnace art, carburizing furnaces and the like will typically deposit carbon soot about the furnace and, in time, the soot will interfere with the carbon process, i.e. shorting of the electrical heating mechanisms or simply interfering with the gas disassociation process. To avoid this, the furnace is periodically heated, usually at an elevated temperature and flushed with oxygen so that the elemental carbon and oxygen will react to produce a carbon bearing gas (i.e. $CO_2$, CO), which is exhausted. Probe manufacturers use the same concept. A solenoid valve admits a stream of oxygen about the probe to burn out the carbon soot collected on the exterior surface of the electrolyte to "restore" the sensor. In practice, the sensor is not fully restored to its original life. The probe's readings foul quicker and quicker requiring more and more frequent burnouts and the probe is eventually replaced because of inconsistent readings.

SUMMARY OF THE INVENTION

Accordingly, it is a principal object of the invention to provide an oxygen sensing arrangement which improves upon the prior art discussed above.

This object along with other features of the invention is achieved in a system that measures the oxygen content of a gas, preferably an industrial furnace gas, by means of a solid, gas sensing media having an interior surface and an exterior surface sealed from one another with a reference gas, such as air, supplied to one of the surfaces and the gas to be sensed, i.e. the furnace gas, supplied to the other surface. A sensing mechanism is provided for receiving an electrical signal from the sensing media which is indicative of the oxygen content of the sensed gas. The improvement in the system includes an air mechanism for directing air flow against the sensing media's surface which is in contact with the furnace gas and an adjustable electrical power supply having output leads connected to the sensing media's interior and exterior surfaces. A switch arrangement is provided for disabling the sensing mechanism when activating the power supply to cause electrical current to flow through the sensing media and heat the sensing media to a predetermined temperature while simultaneously activating the air mechanism so that air flows about and reacts with solid furnace gas depositions on the sensing media's heated surfaces to remove same during a burn out cycle which visibly cleans the probe to its original state while almost completely restoring the probe to its original life.

In accordance with a more specific feature of the invention, the sensing media is a conventional electrolyte. The interior electrolyte's surface is contacted with reference air and a contact anode extends therefrom. The exterior electrolyte's surface is exposed to furnace gas and a cathode contact extends therefrom. The power supply is an adjustable DC voltage which, when inputted to the contacts, reverses its polarity at least once during the described burnout cycle and, more specifically, polarity is reversed for about ¼ the time period of the burnout cycle to restore the surface of the electrolyte to its original state thus extending the life of the sensor.

In accordance with another important aspect of the invention, the arrangement includes a conventional, atmosphere type EGR oxygen sensor having a generally cylindrical slotted shield at one end thereof, a threaded collar adjacent the shield and a generally cylindrical stem adjacent the threaded collar at the opposite end for collecting reference air at the inner surface of the electrolyte. A sensor housing is provided for the oxygen sensor which has a gas tap inlet extending from one of its axial ends. The sensor housing has a gas chamber extending from the housing tap inlet axial end to a probe inlet plate at the gas chamber's opposite end. The probe inlet plate has a centrally positioned threaded opening extended therethrough for sealing engagement with the oxygen sensor's threaded collar. A centrally positioned orificing plate within the housing divides the gas chamber into an inlet chamber extending between the orificing plate and the housing axial end containing the gas tap inlet and a sensing chamber extending between the orificing plate and the probe inlet plate. An outlet is provided in the sensor housing in fluid communication with the sensor chamber. The orificing plate has a plurality of apertures extending therethrough and spaced about an imaginary circle having a diameter at least equal to that of the cylindrical stem of the oxygen sensor so that furnace gas supplied at a regulated flow to the inlet chamber undergoes a pressure drop through the apertures to uniformly disperse the furnace gas in a non-turbulent manner about the oxygen sensor's stem to obviate any concentration of carbon deposition about the outer surface of the electrolyte and materially extend the time between probe burn out cycles.

In accordance with another important feature of the invention, specifically applicable to an endothermic, gas generator application, the automotive type sensor is supplied with an internal resistance heater to which is applied a predetermined voltage. A tap conduit connected to the tap inlet extends from the main conduit at a fixed, predetermined distance which in combination with an adjustable flow meter at the exhaust outlet of the sensor housing is sufficient to reduce the temperature of the endothermic gas sample to temperatures within the range of ambient air temperature to a maximum temperature of about 200°-300° F. The flow of the gas sample established by the flow meter in combination with the temperature of the gas sample and further in combination with the voltage level inputted to the resistance heater results in the temperature of the gas sample raised to a value whereat the oxygen probe produces consistent readings while maintaining the gas sample at a temperature (typically in the order of 900° F. or less) which is less than that at which carbon deposition occurs while the gas chamber flow arrangement positively prevents ambient air from entering the sensing chamber. Thus, the carbon deposition problem is minimized by eliminating its formation at the oxygen sensing probe while also insuring that the probe maintains consistently accurate readings.

In accordance with a yet another specific feature of the invention, the sensor housing includes an air chamber extending from the probe inlet plate to the opposite axial end of the sensor housing and a plurality of small apertures are provided through the housing to permit ambient air to enter the air chamber in a quiescent state. The oxygen sensor probe's internal resistance heater heats the sensor housing and the ambient air in a quiescent state within the housing at the interior surface of the electrolyte is maintained at approximately the same temperature as the furnace gas in contact with the exterior electrolyte surface to improve the consistency of the readings produced by the oxygen sensor.

In accordance with still another aspect of the invention, when the arrangement discussed above is applied as an oxygen sensing arrangement for sensing the composition of furnace atmosphere within a furnace, there is provided a ceramic tube which sealingly extends into and out of the furnace casing and the gas chamber of the sensor housing is mounted to the tube outside of the furnace with the air chamber of the sensor housing positioned in ambient atmosphere. A riser attached to the exhaust outlet and vented either to stack or ported back into the furnace chamber functions as a manometer to insure a draw of furnace atmosphere to the gas tap inlet thus obviating the need of a gas pump. The automotive type oxygen sensor probe mounted within the sensor housing can operate in the manner described without activating the internal resistance heater to provide an economical, long life probe. Alternatively, a water jacket can optionally be provided about the exterior of the ceramic tube to drop the furnace atmosphere gas to a low temperature to prevent carbon deposition and the internal resistance heater of the probe activated to produce a system functionally equivalent to the gas generator arrangement discussed above with all the benefits thereof.

It is thus a principal object of the invention to provide an oxygen sensing system which avoids the problem of premature failure from carbon deposition.

It is yet another major object of the invention to provide an oxygen sensor arrangement which produces consistently reliable readings.

It is yet another object of the invention to produce an economical system for controlling a furnace gas atmosphere.

Yet another object of the invention is to provide an oxygen sensing arrangement which can be used to control the atmosphere of an external furnace gas generator and also function as an in situ furnace atmosphere oxygen sensor.

It is another object of the invention to provide an oxygen sensing system which positively prevents ambient air from being mixed with the sensing gas.

Still yet another object of the invention is to provide an improved burn out method for an oxygen sensing probe.

It is yet another principal object of the invention to provide an oxygen sensing probe with an improved carbon burnout arrangement which increases probe life.

Yet another specific object of the invention is to provide an oxygen sensing system for use with an endothermic gas which produces consistent readings over a wide operating range so that a gas generator system employing the sensor can be operated over a wider turndown ratio than heretofore possible.

Still yet another object of the invention is to provide an oxygen sensing system for an endothermic gas used in a heat treating furnace which generates electrical signals at the same or similar ranges as existing prior art sensing devices to permit the oxygen sensing arrangement of the invention to be readily retrofitted to existing control systems.

Still yet another feature of the invention is to provide an oxygen sensing system particularly for use in sensing endothermic gas used in heat treat furnaces which, compared to prior art devices, is characterized in that it is contained in a simple housing which does not need externally applied heaters or other sensor control arrangements other than the actual sensing device itself and thus is more economical and less costly to assemble and maintain than the prior art devices.

Still another object of the invention is to provide a gas sensor system for use in sensing the oxygen content of an industrial furnace gas which provides simple and economical means to drop the temperature of the furnace gas to temperature ranges prior to that at which carbon deposition occurs before the furnace gas is sampled.

It is yet another object of the invention to provide a simple and economical oxygen probe arrangement.

Yet another object is to provide an atmosphere sensing system to determine oxygen levels in atmospheres using hydrogen and nitrogen with or without the presence of carbon.

These and other objects of the invention will become apparent to those skilled in the art upon a reading and understanding of the detailed description set forth in the section which follows.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein:

FIG. 8 is an electrical schematic similar to FIG. 7 showing an alternative embodiment of the switching circuit used for burn out of a titanium, oxygen sensor probe.

DETAILED DESCRIPTION OF THE INVENTION

A. Gas Generator Application

Figure 1:
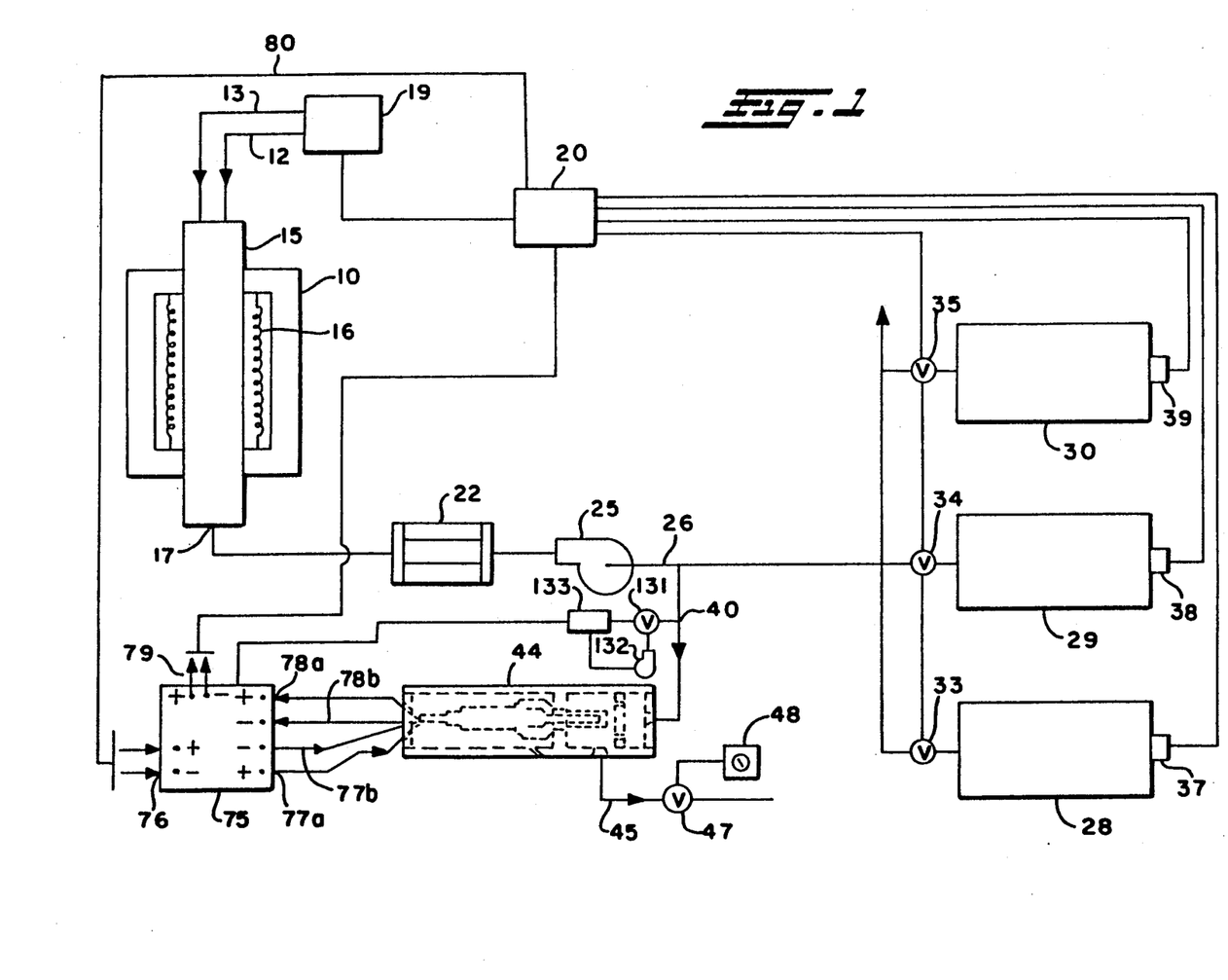
FIG. 1 is a schematic illustration of an endothermic gas supply system for use in heat treat furnaces which employ an external gas generator.

Referring now to the drawings wherein the showings are for the purpose of illustrating a preferred embodiment of the invention only and not for the purpose of limiting same, FIG. 1 shows a schematic illustration of an external endothermic gas generator—heat treat furnace arrangement. This arrangement or system includes an external gas generator 10 which functions as a source of generating an endothermic gas of preferred composition. Generator 10 is preferably of the type marketed under the brand name designation "RX" by Surface Combustion, Inc., the assignee of the present invention. As is conventionally known with respect to tho operation of generator 10, combustion air through line 12 is reacted with natural gas through line 13 through a catalytic bed 15 which is typically electrically heated by heating element 16 to an elevated temperature such that at the exit end 17 of generator 10 an endothermic gas is produced at a temperature of between 1900°-2200° F., typically 1950° F. The endothermic gas or carrier gas produced is generally defined by the American Society for Metals as one of a series of atmospheres designated as class 300 carrier gas typically having approximate compositions of 40% nitrogen, 40% hydrogen and 20% carbon monoxide. A typical analysis would be as follows:

40.4% $H_2$
19.9% CO
39.0% $N_2$
0 to 0.4% $CH_4$
0.2% $H_2O$
0.1 to 0.5% $CO_2$.

The catalyst bed typically comprises nickel based catalyst lumps which are interposed between beds of inert lumps of heat transfer particulates such as $AL_2O_3$. Reference should be had to Schultz U.S. Pat. No. 4,805,881 (incorporated herein by reference) for a more definitive explanation of an endothermic gas generator and the reversible reactions which can and will occur with endothermic gas. For purposes of this specification, it should be sufficient to note that carbon monoxide will disassociate at certain temperatures to carbon and carbon dioxide and that hydrogen and carbon monoxide will react at certain temperatures to produce water vapor and carbon. More specifically, at temperatures of about 1400° down to about 900° F. it is possible for the carrier gas to disassociate and produce deposits of elemental carbon.

An alternative to the natural gas generator disclosed in FIG. 1 is an external methanol generator which mixes nitrogen and methanol in a vaporizer with the vaporized methanol and nitrogen mixture reacted in a catalyst filled retort such as disclosed in Schultz U.S. Pat. No. 4,249,965, incorporated also by reference herein. No matter which form the generator may take, the gas produced is a function of a time-temperature relationship and a valve train 19 regulates the fixed air-fuel ratio and flow rate of air and gas through lines 12 and 13 into generator 10. Valve train 19 as well as the heating element 16 of generator 10 are in turn controlled through a master microprocessor controller 20 which controls the overall operation of the entire process. Such a controller is manufactured and marketed by Surface Combustion, Inc., the assignee of the present invention, under the brand name "CASEMATE". Other controllers such as a 560 controller manufactured by Barber-Colman Co. can be used.

As already noted, the exhaust temperature of the carrier gas leaving generator 10 is anywhere between 1900°–2200° F. and at temperatures between 1400° all the way down to approximately 900° F., carbon deposition will occur. Because generator 10 is located remote from the furnaces, heat loss will naturally occur through the duct work, even insulated duct work, and will drop the temperature of the endothermic gas into the carbon deposition range. For this reason, and because of difficulties associated with moving gas at high temperatures, the endothermic gas immediately after leaving gas generator 10 is passed through heat exchanger 22 whereat its temperature is dropped to anywhere between 200°–400° F. depending upon the gas flow rate. Thus, the endothermic gas is dropped below the temperature at which disassociation of its various elements will occur. Inherently, when the endothermic gas is dropped in temperature, some trace amount of carbon will precipitate and the actual amount of elemental carbon produced is dependent on the time the gas is within the aforesaid temperature range. Thus, no matter what is done at the sensor to minimize carbon deposition, it has to be realized that some carbon "trace" is carried with the gas stream exiting heat exchanger 22.

The reduced temperature endothermic gas is pressurized as by blower 25 and passed by main conduit 26 into a plurality of heat treat furnaces, preferably carburizing furnaces, there being three such furnaces 28, 29 and 30 shown in FIG. 1. Heat treat furnaces 28–30, which are capable of performing carburizing heat treat processes are conventional and such furnaces are sold by Surface Combustion, Inc. under the brand name "ALLCASE". As is well known, the endothermic gas is metered into furnaces 28–30 through respective valves 33–35 and the temperature of each of the furnaces 28–30 is controlled by burners or electrical heating elements 37, 38 and 39 respectively. Firing of burners 37–39 and actuation of valves 33–35 are also controlled by controller 20. It should be understood that the quantity of endothermic gas produced in generator 10 varies as a function of the demand for the gas by each furnace 28–30 and that the gas required is dependent upon what time the particular furnace 28–30 happens to be at in the carburizing cycle. Obviously, at the onset of the cycle, a large quantity of endothermic gas is required whereas the requirement is continually reduced as the carbon is deposited and absorbed into the case of the workpieces. Controller 20 must then turndown or reduce the volume of endothermic gas produced and supplied to furnaces 28–30. As used herein, the reduction in output from the maximum capacity of generator 10 is referred to as the turndown ratio. Thus, if the system had a turndown ratio of 2:1, it would mean that the output of gas generator 10 could be reduced from a maximum flow to a minimum flow which is 50% of the value of the maximum flow. The conventional external generator has a turndown ratio of 2:1 and this explains the reason why the gas temperature leaving heat exchanger 22 can vary from 200°–400° F. Finally, because natural gas and combustion air is flowing over a catalytic bed in generator 10, some mechanism has to be provided for adjusting heater 16, flow rates through valve train 19, etc. to insure that the endothermic gas reaction proceeds to completion. This is typically done by measuring the oxygen content of the endothermic gas and adjusting generator 10 by controller 20. The oxygen content for a rich or reducing gas is typically sensed in parts per million (ppm) and by means of conventionally developed heat entropy formulae is converted into a $CO_2$ composition or dew point (water vapor) readings which control the process. The formulae are expressed as algorithms in microprocessor controller 20. Those algorithms as well as algorithms converting the analog signal developed by the oxygen sensor probe (to be described hereafter) to in turn develop control signals outputted by controller 20 are all conventional and will not be described further in detail herein and do not, per se, form part of the invention. Up to this point, all items discussed thus far are conventional and well known in the art.

As noted above, blower 25 develops a positive pressure (above standard atmosphere) of 10–12 inches water column in main conduit 26. A small tap conduit 40 ($\frac{1}{4}"$ threaded pipe fitting and $\frac{1}{4}"$ line) directs a sampled gas stream of the cooled endothermic gas to an oxygen sensor housing 44. Oxygen sensor housing 44 is positioned at a distance remote from main conduit 26 such that the temperature of the endothermic gas in tap conduit 40 will naturally decrease through indirect heat transfer vis-a-vis tap conduit 40 with air at ambient temperature. More specifically, temperature of the sample gas stream entering housing 44 will decrease from a main conduit 26 temperature of 200°–400° to a temperature anywhere between approximately ambient air temperature to 200° F. and the length of tap conduit 40 is predetermined so as to produce this temperature drop. The sampled stream of endothermic gas transferred to sensor housing 44 by tap conduit 40 exits sensor housing 44 through flare conduit 45. A conventional metering valve 47 and an adjustable conventional flow controller 48 is provided to control the flow rate of the "spent" sampled gas at a value of 1–2 cu. ft/hr and importantly establishes a back pressure in sensor housing 44. That is, valve 47 establishes a positive pressure of the gas sample stream within oxygen sensor housing 44 which prevents any infiltration of ambient air into sensor housing 44 through flare conduit 45. Also, by controlling the back pressure, compensation is provided for variations in pressure in main conduit 26 to assure that an accurate tap of a sampled stream from main conduit 26 occurs. This allows a wider turndown ratio of gas generator 10. Turndown ratios as high as 5 and 6 to 1 are possible with the present invention since the flow controller 48 will automatically adjust to set the appropriate flow rate through valve 47 and establish an acceptable back pressure through sensor housing 44. In the prior art device disclosed in the '807 patent, a plurality of radial outlets is required to provide symmetrical flow and if downstream valving were employed, valve mis-timing would adversely affect the flow about the sensor. The endothermic gas generator system of the invention as thus far described, provides an arrangement which assures a positive flow of the gas stream sample at a set pressure and at a reduced temperature for reasons which will be explained in further detail hereafter.

Figure 2:
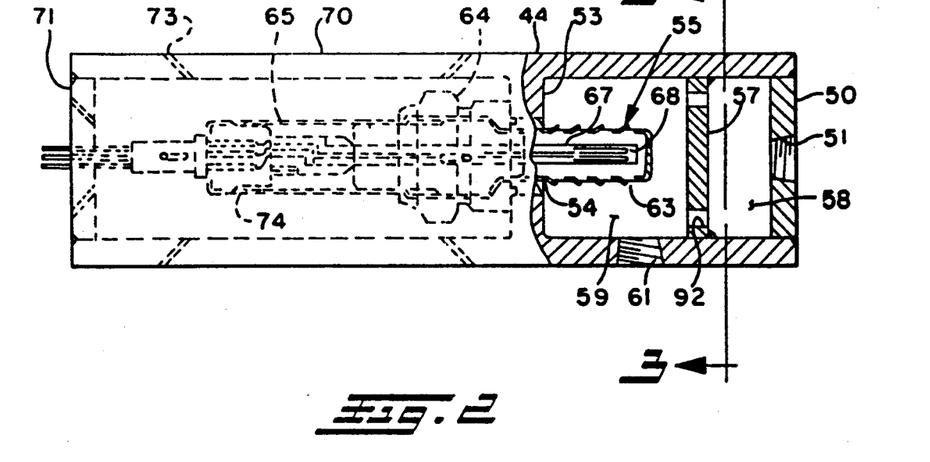
FIG. 2 is an elevation view partly in section of the oxygen sensor and housing which is used in the oxygen sensing arrangement of the invention.

Referring now to FIGS. 1 and 2, sensor housing 44 is cylindrical and closed at its axial ends to define a sealed gas chamber therein. At one axial end 50 of housing 44 is a tap inlet 51 which receives a threaded fitting for tap conduit 40. At the opposite axial end of the gas chamber is a probe inlet plate 54 which has a centrally positioned threaded opening for sealing receiving an oxygen sensor 55. In between axial end 50 and probe inlet plate 53 is a circular orificing plate 57 which divides the gas chamber of sensor housing 44 into an inlet chamber 58 extending between orificing plate 57 and axial end 50 and a sensing chamber 59 extending between orificing plate 57 and probe inlet plate 53. A threaded exhaust outlet 61 sealingly receives a fitting from flare conduit 45 and extends through the cylindrical surface of housing 44 to provide fluid communication with sensing chamber 59.

Figure 7:
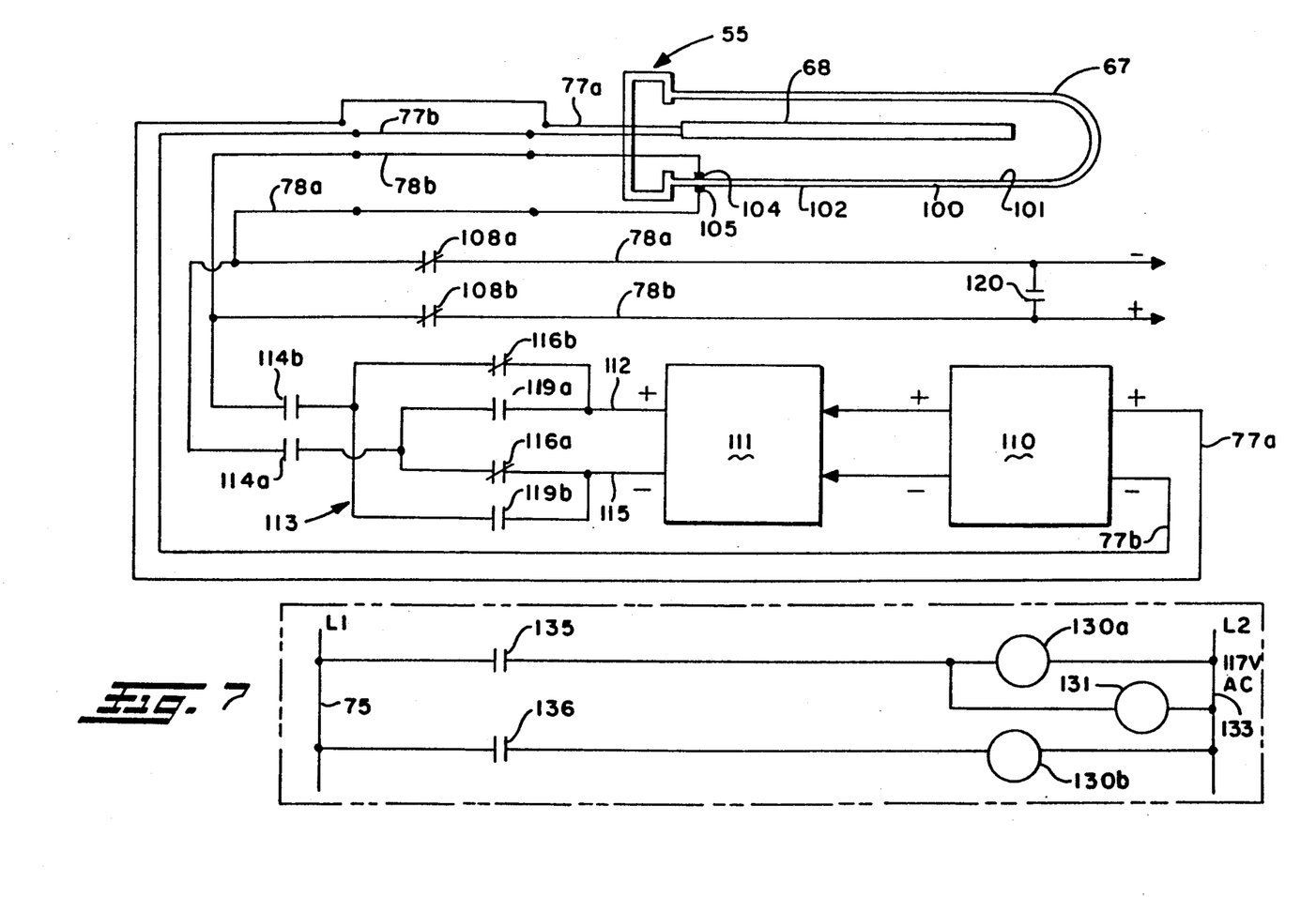
FIG. 7 is an electrical schematic of the switching circuit used for burn out of a solid, electrolyte probe.

Oxygen sensor 55 is a one piece oxygen sensing probe which is currently used in the automotive field to sense the oxygen content of the exhaust gas from the engine. In response to lean or rich exhaust fume readings sensed by the probe, adjustments to the fuel-air ratio in the automobile's engine injector's are made vis-a-vis a pollution control system commonly referred to as EGR (exhaust gas recirculation). A number of automotive oxygen sensing probes are available and sensor 55 used in this invention and which is the sensor used to generate the data referred to hereafter, is a sensor supplied by NTK Co. Ltd. of Japan to Chrysler Corporation and available from Chrysler Corporation as Mopar Part No. 5233088. This sensor has four leads extending from its stem as shown in FIG. 7. Alternatively, a sensor manufactured by NTK Co., Ltd. of Japan and available from Chrysler Corp. under Mopar Part No. 5227368 which as three leads can also be used. Both oxygen sensor probes use a stabilized zirconium electrolyte to generate an EMF signal and both employ internal platinum resistance heaters. While the invention has been successfully tested with zirconia electrolyte oxygen sensor probes, it is believed that the invention will also work with titania oxygen sensor probes in which the resistance of the probe varies in accordance with the oxygen concentration sensed. A titanium probe which is believed acceptable is available from the Autolite Division of Allied Automotive under Part No. 52002106. However, fast data for titania sensor probes have not been developed.

Sensor 55 conventionally includes a cylindrical slotted shield 63 at one end which terminates in a threaded collar 64 which in turn terminates in a porcelain, generally cylindrical stem 65 from which extend electrical leads 66. Collar 64 is threadingly received within probe inlet probe 54 so that slotted shield 63 is centrally positioned within sensing chamber 59. Slotted shield 63 contains a sealed electrolyte cell 67 of stabilized zirconium shown diagrammatically at 67 which extends into cylindrical stem 65 in a conventional manner. Also, within slotted shield 63 and either within or about electrolyte cell 67 is a platinum resistance wire heater shown diagrammatically at 68. It should be noted that shield 63 which contains a stem or shield of platinum encased zirconia is of a short length since the shield must fit within the exhaust manifold and conventional thinking within the furnace art, promulgated by furnace probe suppliers, is that the short length of the electrolyte in the automotive probe renders the probe unsuitable for furnace application.

Sensor housing 44 also contains an air chamber 70 which extends from the opposite axial end 71 of sensor housing 44 to probe inlet plate 53. Opposite axial end 71 is closed end leads 66 extend therethrough. Air chamber 70 thus surrounds and encapsulates cylindrical stem 65 and threaded collar 64 of oxygen sensor 55. Extending through sensor housing 44 and in fluid communication with air chamber 70 is a plurality of slotted openings 73 which permits ambient air to contact sensor stem 65 in a quiescent state. Sensor stem 65 has at least one opening 74 extending therein to provide fluid communication between ambient air and the inner electrolyte surface.

Insofar as the operation of oxygen sensor 55 is concerned, reference should be had to Bienkowski U.S. Pat. No. 4,147,513 and the patents cited therein, all of which are incorporated by reference herein. In accordance with known theory, the electrolytic cell 67 of stabilized zirconium develops an electrical signal when one side of electrolytic cell 67 is exposed to ambient air through stem opening 74 and the other side of electrolytic cell 67 is exposed to endothermic gas vis-a-vis cylindrical slotted shield 63. The electrical signal is correlated to the oxygen concentration in the endothermic gas (i.e. log of partial pressure of the oxygen at a fixed temperature). The temperature of the endothermic gas is established by the voltage inputted to resistance heater 68. In the present invention, a circuit board 75 (FIG. 1) is used to supply the DC voltage at a predetermined voltage out at 77 to resistance heater 68. The voltage generated by electrolytic cell 67 is sensed by board 75 at 78 and converted to a controller signal at 79 which controller 20 uses to vary the operation of gas generator 10 in a conventional manner. Conventional electrical circuits are used in board 75 to accomplish this.

Figure 4:
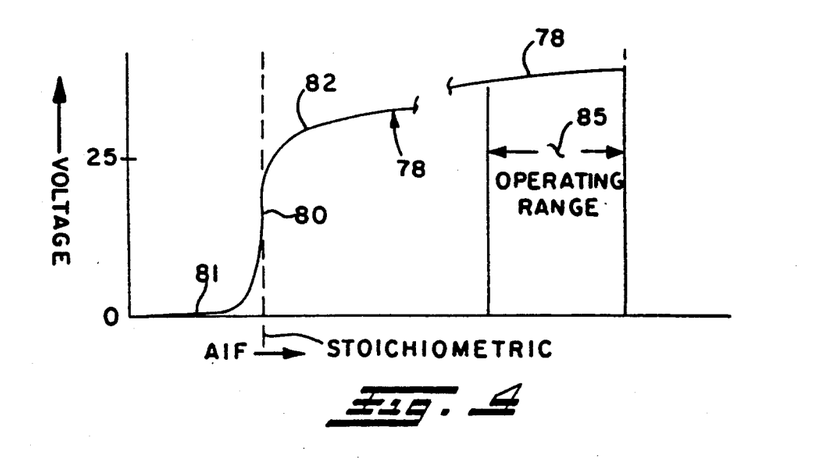
FIG. 4 is a graph showing the voltage output of the oxygen sensor as a function of the air/fuel ratio with lean mixture (i.e. high oxygen) to the left of the stoichiometric shift line and rich mixture (i.e. low oxygen) at the right.

Referring now to FIG. 4, the electrical signal 78 generated by sensor 55 is plotted as a function of the output voltage on the "y" axis correlated to the air to fuel ratio (A/F). In the conventional automotive application, the basic concept is to meter the air-fuel ratio through the injectors into the cylinder heads of the engine at the precise ratio which produces stoichiometric combustion so that acceptable products of combustion are produced in appropriate proportions in the combustion cycle of the engine which can then be burned in the afterburner or catalytic converter to reduce pollution. Thus, an automotive oxygen sensor must be able to sense and distinguish when the engine is operating lean or with excess air and when the combustion is occurring rich or with insufficient air. This is shown in FIG. 4 where the vertical portion of the curve designated as 80 represents stoichiometric firing while the left hand portion of the curve 81 represents a lean condition and that portion of the curve to the right 82 of the stoichiometric portion 80 represents a rich firing condition. Thus, assuming a constant fuel quantity for the air to fuel ratio plotted, the air quality of the ratio is decreasing to the right on the "x" axis. In the automotive application, a DC voltage of 12–14 volts is applied to heater 67 and the sensor develops an output voltage of 5–25 millivolts when the rich fume concentration is sensed and 0 volts when a lean condition is sensed. It should be noted that the signal generated by 5 volts is significant and the transition between lean and rich, i.e. stoichiometric, is very sharp. This permits the sensing mechanism to easily "hunt" in on the preferred ranges. In contrast, the operating range of the present invention is to the far right (indicated by the curve being broken) of the stoichiometric shift point 80 shown in FIG. 4 and the output is measured in millivolts and the voltage applied to the sensor is increased from 12-14 volts to about 21 volts DC. The voltage increase does two things. First, it raises the internal resistance heater output which is at a value of about 800 to 1600 (typically 1200) ohms and increases the temperature at which the endothermic gas is heated from that which the internal heater 68 heats the exhaust gas in a normal automotive application. More specifically, for the 1-2 cu. ft/hr flow rate and with a gas inlet temperature anywhere between ambient air temperature and a maximum of about 250° F., heater 68 at its boosted output will heat the endothermic gas to temperatures of approximately anywhere between about 400° F. to a maximum of about 800° F. At this temperature, which is significantly less than that of prior art probes used in the heat treat art, carbon deposition will not occur. At the same time, however, the temperature increase of the endothermic gas effected by the boosted heater output is sufficient to lower the resistance of the electrolyte cell (i.e. resistance decreases as temperature increases) to a value which is consistently measurable. Further, while the voltage input to heater 68 is increased, premature heater failure has not been observed.

Figure 5:
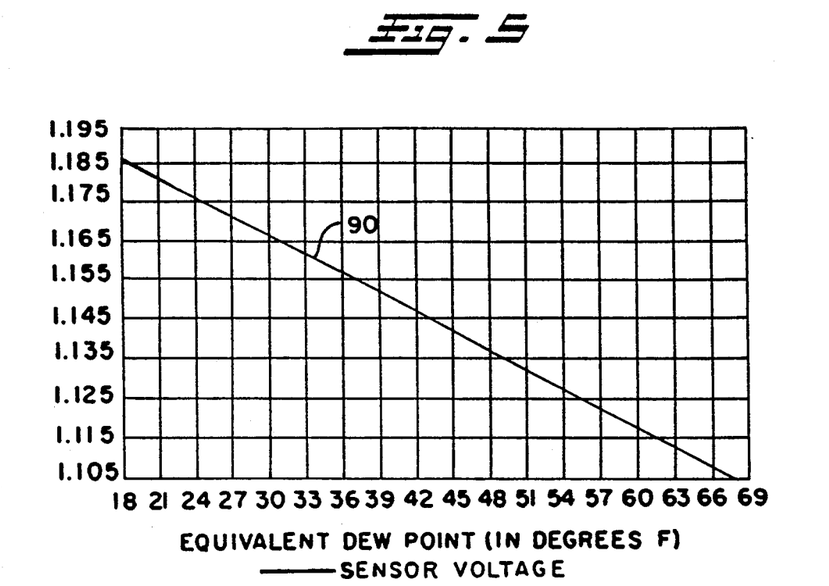
FIG. 5 is a graph of the output signal of the oxygen sensor in millivolts versus the dew point concentration of the sensed gas for both the prior art probe and the probe of the present invention.
Figure 6:
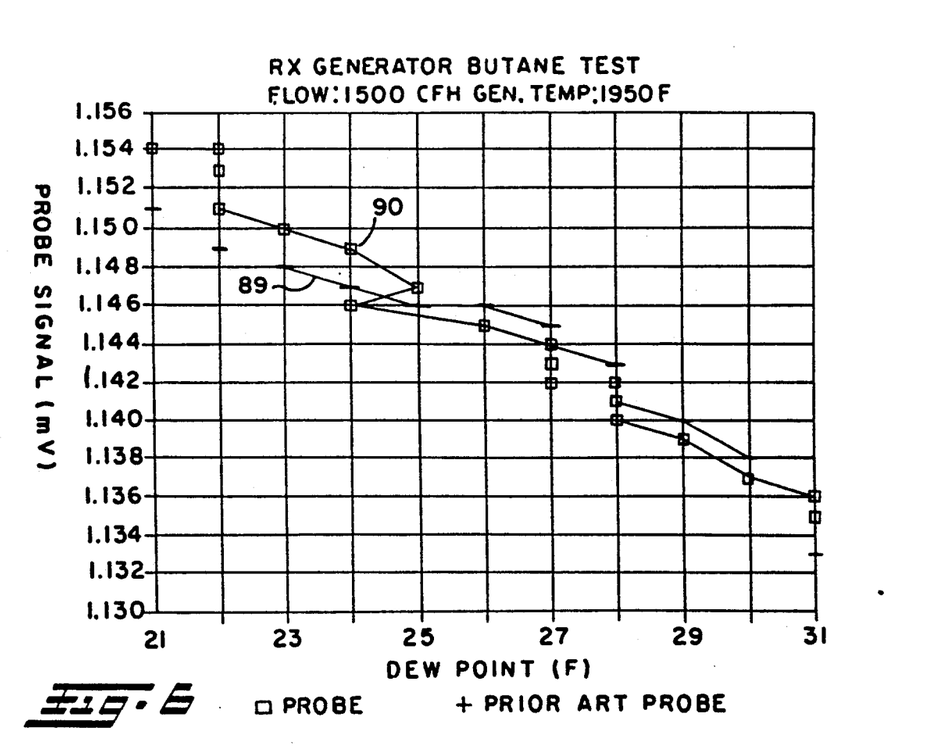
FIG. 6 is a graph similar to FIG. 5 but correlating the dew point in degrees Fahrenheit of the endothermic gas to the millivolt output of the oxygen sensor probe used in the present invention.

Referring now to FIGS. 5 and 6, there is shown the output voltage in volts on the "y" axis plotted as a function of the dew point of the gas on the "x" axis. FIG. 5 represents the NTK 5233088 oxygen sensor probe and is the final millivolt range established for the sensor. FIG. 6 represent test data of a prototype NTK 5227368 oxygen sensor probe and is shown to give a comparison of the millivolt output shown by "square" readings of the invention with a "T" reading of the probe described in the '807 patent. FIG. 6 shows that the probe of the present invention is as consistent as that of the existing probes used in the heat treat field and develop similar electrical signals. Thus, the probe of the present invention can be applied to existing installations without modifying electrical circuitry of existing controllers and conversion to a non-carbon sooting arrangement is easily accomplished. Further, tests on an experimental probe of the present invention have shown that even with the increased voltage applied to the conventional automotive oxygen sensor, in an environment where the probe is operated continuously 24 hours a day, the probe generated consistent readings over a six month time span for the same application where the prior art probe was failing and requiring clean-out within a period of several weeks.

It can or should be recognized from the above discussion concerning FIG. 4 and the graphs shown in FIGS. 5 and 6 that oxygen sensor 55 is being operated at a range where very fine and discrete changes in resistance of the electrolyte cell are being utilized to control the entire gas generating process. Accordingly, it is imperative that consistency and reliability be achieved by maintaining consistent control of the environment under which oxygen sensor probe 55 is exposed to gases which it senses. Insofar as the endothermic gas is concerned, it is important that the gas uniformly impinge slotted shield 63 at a consistent flow and, of course, at a controlled temperature below that which the gas is raised to by heater 68. In the present invention, consistent uniform flow is achieved by a pressure drop arrangement formed in orificing plate 57. More particularly, and with reference to FIG. 3, the pressure drop arrangement includes providing a plurality of equally spaced apertures 92 formed in plate 57 about an imaginary circle 93 which has a diameter slightly greater than the diameter of slotted shield 63 of oxygen sensor 55. In the preferred embodiment apertures 92 are approximately $\frac{1}{8}"$ in diameter and tap inlet opening is sized to receive a $\frac{1}{4}"$ pipe thread. Sizing between tap inlet 51 and apertures 92 produce a pressure drop through apertures 92 with the amount of the pressure change in turn controlled by the downstream valving arrangement 47, 48. Apertures 92 meter fine, nonturbulent streams of endothermic gas which uniformly penetrate and surround slotted shield 63 to provide a non-turbulent flow of gas about electrolyte cell 67 producing consistent readings therein. Further, the flow is adjustable by flow controller 98 to zero out or calibrate oxygen sensor 55. Thus, downstream valving arrangement 47, 48 not only prevents ambient air from entering sensing chamber 59 but also controls the "fixed" pressure drop arrangement established by tap opening 51 and apertures 92 to produce uniform dispersion of the endothermic gas about electrolyte cell 67 in a non-turbulent manner.

In addition to this feature of the invention, air housing portion 70 insulates cylindrical stem 65 of sensor 55 to equilibriate the temperature of sensor stem 65 with that of slotted shield 63. That is, the temperature of ambient air through opening 94 sensed in stem 65 approximates the temperature of the endothermic gas sensed at slotted shield 63 since the heat from internal heater 68 will eventually heat both stem 65 and shield 63 and the ambient air will not cool stem 65 because of extension housing portion 70. In this connection, apertures 73 restrict the flow of ambient air into and out of air chamber 70. That is, the air is in a quiescent state and thus capable of being equilibriated to the temperature of the endothermic gas. It is known in the art that while temperature has absolutely no bearing on the oxygen content of ambient air, temperature differential can result in varying sensor readings due to varying resistances established at the juncture of the electrodes or contacts with the electrolyte cell and the problem has been deemed sufficiently severe to cause special precautions to be placed in the readout circuitry in an attempt to artificially compensate for the temperature change. The problem is defined and explained in Capone U.S. Pat. No. 4,784,728 incorporated by reference herein and Bienkowski '513. As noted, air extension housing portion 70 encapsulates and shields stem 65 and the system maintains the endothermic gas at a low temperature so that heater 68 is providing the entire heat to the entire sensor 55. Thus, ambient air temperature approximates the sensed endothermic gas temperature and there is no temperature variation at the contacts to distort the oxygen sensing probe readings.

In summary of some of the features of the invention described thus far, it is to be noted:

(a) The combination of the gas chamber, its single inlet 51 and outlet 61 arrangement coupled with flow meter 47, 48 positively prevents air from inadvertently being drawn into sensing chamber 59 and adversely distorting oxygen sensor probe readings.

(b) In combination with the positioning of the sensor housing 44 and the flow dispersion through gas chamber is the realization that (i) consistent, discernible output readings from the oxygen sensor probe can be had with the internal heater, alone, being sufficient to drive the temperature of the endothermic gas to a temperature range which the probe can sense and (ii) this temperature range, unlike all other furnace oxygen sensor probes, is low enough to prevent carbon precipitation from occurring within the probe, thus providing a dramatic increase in the life of the oxygen sensor probe.

(c) By enclosing the stem of the oxygen sensor probe in air chamber 70 to produce generally quiescent air in air chamber 70, temperature variations on the contact lead is minimized to produce consistent probe readings.

Figure 3:
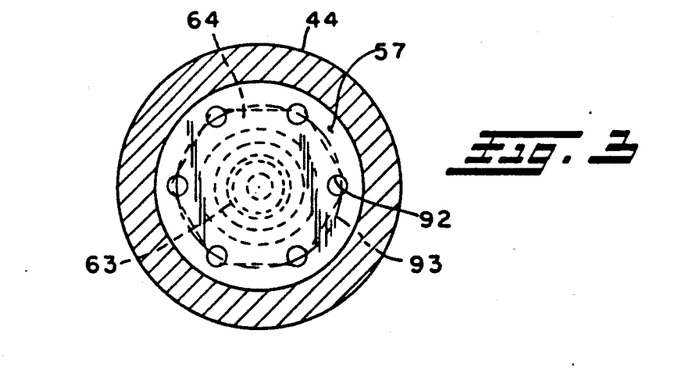
FIG. 3 is a drawing of the oxygen sensor housing taken along line 3—3 of FIG. 2.

(d) By using orificing plate 57, not only is the electrolyte uniformly exposed to an "even" concentration of the endothermic gas, but should there be carbon particles in the gas stream, the carbon particles will not concentrate over any particular area of the probe's surface which has been found to occur in the prior art probes.

A concentration of the carbon on the probe's surface destroys the consistency of the probe. Thus, assuming some carbon particles in the gas sample stream, the present invention distributes the particles evenly about the probe's surface preventing any local concentration causing premature failure.

As noted above, when the endothermic gas produced in gas generator 10 drops in temperature through heat exchanger 22, some trace particles of carbon are precipitated. While the present invention prevents further carbon deposition, eventually the trace carbon particle will coat oxygen sensor probe 55 and foul it. Furthermore, it is believed that trace elements of other chemicals in the gas produce solid deposits on the probe which can also affect probe readings. However, the arrangement as described thus far extends the life of the probe in the magnitude of 15 to 20 times. For example, in one prototype test, a sensor believed constructed in accordance with the teachings of the '807 patent fouled in about three weeks while the prototype sensor did not foul after six months. In another sensor, installation in which a sensor believed constructed in accordance with the '807 typically fouled within one to two days, the sensor arrangement described thus far had a life between one to two months.

When the oxygen sensor probe 55 does become fouled with carbon, attempts have been made in the prior art to burn out the carbon in a conventional manner. This is typically accomplished by heating oxygen sensor probe 55 to temperatures well in excess of 1600° F. and flooding the probe's exterior electrolyte's surface with air to cause the carbon and oxygen, at elevated temperature, to combine into $CO_2$ which is then exhausted from the probe. The probe must then cool down for its temperature to stabilize. The entire process takes several hours and this is too long a time period for the generator to run at a fixed setting and too long for the furnaces to be shut down. In addition, it is noted that the burn out achieved in the conventional burn out cycle did not fully clean the probe's surface. Deposits, possibly sulfur or other trace elements from the gas, were still present and the life of the probe was not restored to its original life. Further, the probe life was successfully reduced between burn outs. To address such problems, the arrangement disclosed in FIG. 7 (an alternative embodiment is disclosed in FIG. 8) has been developed.

THE BURN OUT APPLICATION

B. Burn Out

Referring now to FIG. 7 (and FIG. 1), there is shown in schematic form automotive oxygen sensor probe 55 which is an NTK No. 5233088 automotive zirconia sensor. The electrolytic cell 67 uses a solid electrolyte 100 (stabilized zirconia) which has a noble metal, i.e. platinum, bonded to its inner surface 101 and a noble metal, i.e. platinum, bonded to its outer surface 102. The platinum attached to inner and outer surfaces 101, 102 form a sheath which insures inner and outer surfaces 101, 102 are sealed from one another. At the inner electrolyte surface 101 is an anode contact or electrode 104 to which is secured sensor output lead 78b. At the outer electrolyte surface 102 is a cathode contact or electrode 105 to which is secured sensor output lead 78a. As shown in FIG. 1, sensor output lead 78a, 78b extend into circuit board 75 and from there are inputted at 79 to microprocessor controller 20. Within circuit board 75 is a normally closed relay contact or switch 108a connected to sensor output line 78a and a normally closed relay contact or switch 108b connected to sensor output line 78b. As noted, contacts 108a, 108b are normally closed so that the Emf generated between inner and outer electrolyte surfaces 101, 102 can be inputted to microprocessor controller 20. As will be explained shortly, contacts 108a, 108b are open to disable the sensing circuit and a capacitor 120 (nominally 0.1 u f use F at 50 volt direct current) is provided between lines 78a, 78b to prevent transient voltage from being transmitted to microprocessor controller 20 when contacts 108a, 108b are opening or closing.

Input leads 77a, 77b are connected to internal resistance heater 68 in oxygen sensor probe 55 and are powered by a 15-25 volt DC power supply 110 which is under control of microprocessor controller 20 through line 80. As noted above, output voltage from power supply 110 is typically set at about 18 volts to produce desired heating from resistance heater 68. Output from power supply 110 also passes through an adjustable current supply 111 which has a range typically of about 20-80 milliamps. The positive terminal from adjustable current supply 111 connects on line 112 through a switching circuit 113 past normally open contact relay 114b to anode contact 104. The negative terminal of adjustable current supply 111 connects on line 115 through switching circuit 113 past normally open contact relay or switch 114a to cathode contact 105. Switching circuit 113 includes normally closed contact relay or switch 116b which normally connects positive terminal line 112 to normally open contact 114b and normally closed relay contact or switch 116a which connects negative terminal lead 115 to normally open contact 114a. Normally open contact relay or switch 119a is provided for connecting positive terminal lead 112 to normally open contact 114a while normally open relay contact or switch 119b connects negative terminal lead 115 to normally open contact 114b. When contacts 116a, 116b are open and contacts 119a, 119b are closed, polarity from adjustable current supply 111 to anode contact 104 and cathode contact 105 is reversed.

Referring to the lower portion of FIG. 7 and FIG. 1, a three way solenoid valve 133 under the control of microprocessor controller 20 at a predetermined time period closes normally open contact 130a which in turn opens the valve motor on valve 131 and actuates air pump 132 to port completion air into the gas chamber of sensor housing 44. At the same time, normally open contact 130b is also closed. Solenoid valve 133 is biased to close contact 135 which establishes biasing voltage to open normally closed contacts 108a, 108b and close normally open contacts 114a, 114b. Current then passes from contact anode 104 through solid electrolyte 100 to cathode contact 105 and in the process thereof heats solid electrolyte 100 within a short time to temperatures in excess of 1500° F. It is not precisely understood what exactly happens to solid electrolyte 100 when current is passed through the electrolyte (although at least one plausible theory can be advanced). It has been verified by tests that the electrolyte 100 reaches a high temperature at which burn out of carbon deposits readily occurs (as well as other deposits capable of oxidation such as sulfur) in a relatively short time period of several minutes, typically four to five minutes. Further, when the current ceases to be applied to solid electrolyte 100, the electrolyte returns to the same sensitivity or range of sensitivity it possessed prior to inputting current through the electrolyte. This is not to say that the ability of the electrolyte to generate consistent Emf voltage readings before and after heating by passing current therethrough retains constant irrespective of the intensity of the current which is passed through the electrolyte. However, at the 20–80 milliamp range disclosed herein, the voltage output of solid electrolyte 100 remains consistent before and after current is passed through the electrolyte.

At a predetermined time period during the burn out cycle, solenoid valve 133 is further actuated to open contact 135 and close contact 136 which, in turn, opens contacts 116a, 116b and closes contacts 119a, 119b to reverse the polarity of adjustable current supply 111 to anode, cathode contacts 104, 105. Reversal of polarity of the current flow through electrolyte 100 during the burn out cycle results in a noticeable, "cleaner" appearance of the exterior surface 102 of electrolytic cell 67 and, thus, polarity reversal during the burn out cycle is the preferred embodiment of the invention. Preferably, polarity reversal occurs for some time period near the end of the burn out cycle, preferably at the ratio of about 1:4. In other words, if current flows from anode contact 104 to cathode contact 105 for four minutes, then the current is reversed in flow for one minute at the tail end of the burnout cycle. Again, this is the preferred operation of the burn out cycle based on observations of probe cleanliness and probe life before burn out cycles have to be repeated. It is within the broader concept of the invention to alternate current flow through electrolyte 100 at various frequencies or even apply alternating current to solid electrolyte 100 during the burn out cycle.

Once the burn out time is completed, solenoid valve 133 is deactivated and the contacts returned to their normal open or closed positions whereat the sensing circuit through output leads 78a, 78b generate analog signals indicative of the oxygen content of the endothermic gas.

The burn out cycle described can be characterized as being extremely short in time duration which means that after burn out, oxygen sensor probe 55 will, within a short period of time, stabilize at its normal operating temperature. Thus, the endothermic gas generator 10 can be left at a fixed setting while burn out of oxygen sensor probe occurs within a total time period of no more than about twenty minutes, i.e. about five minutes for burn out and fifteen minutes for probe stabilization. This will not adversely affect continuous operation of carburizing furnaces 28, 29 and 30. In addition, a secondary benefit of the burn out cycle described is that no external heat is applied to achieve burn out nor does resistance heater 68 have to be excessively heated to produce the burn out temperature. Thus, the life of internal resistance heater 68 is not adversely affected.

The schematic illustrated in FIG. 7 is described with reference to a solid electrolyte for which test data has established the burn out method described. The invention is believed applicable to a titania sensor such as supplied by Autolite as Part No. 53002106 and KA 77-19. An electrical schematic for a titania oxygen sensor probe 55a is illustrated in FIG. 8 and reference numerals in FIG. 7 will likewise apply to describe the same parts and components used in FIG. 8. The automotive oxygen sensor probe 55a in FIG. 8 uses a common sensor signal and heater ground 77b which is shown in FIG. 8 to be connected to the same circuit components as the four lead sensor 55 disclosed in FIG. 7. As is well known, a titania sensor develops varying electrical resistance depending on the oxygen concentration of the endothermic gas. Accordingly, a constant reference voltage of 15 volts DC is inputted at 150 on input lines 78a to the titania resistor and the lead or line resistance is shown schematically at 151. An amplifier 155 then functions as a signal conditioner and scaling device to measure voltage drop through the titania resistor on output leads 78a, 78b connected to microprocessor controller 20. A non-inverting amplifier circuit is shown having a low resistance 156 at the voltage input of amplifier 155 and a degenerative feedback resistance 157 of about 1000 ohms to provide good closed-loop gain characteristics. Capacitors 120 of 0.1 u f, 50 volts DC prevent transient voltage surge when contacts 108a, 108b are opening and closing. The remainder of the circuit shown in FIG. 8 is identical to that described in FIG. 7 and the burn out cycle operates in the same manner to generate heat through the titania to achieve burn out.

The oxygen sensor probe measuring instrument has been designed to operate continuously or under intermittent operation and operates at a temperature substantially lower than the '807 automotive probe. The lower temperature allows the probe to last longer and also reduces greatly the amount carbon that is released from the endothermic gas. The prior art system would accumulate enough carbon over a two day period of operation, that the probe would appear gray to black in color instead of white. This accumulation of carbon has a negative effect on the probe's output signal. The effect will cause probe resistance and probe voltage to change, even though the generator product as was to remain steady in dew point and composition. The prior art probe would go into error because of the accumulation of carbon. The error would then grow greater over a daily basis until the probe would no longer operate. During the period of continued operation, the prior art probe would adjust the generator improperly to a richer condition, as the accumulation of carbon on the probe grew greater and greater.

Within the probe of the present invention, the lowered operating temperature causes the above phenomena to occur at an extremely reduced rate than that of the prior art design. There is, however, a slight accumulation that occurs over a period of thirty days, that can be compared to the prior art's loss of performance, two day period. To overcome this potential problem and slow loss of performance, an automatic circuit has been created to flow ambient atmospheric air through the probe periodically. The flow of air is intended to react with the carbon and form $CO_2$ and thus carry carbon from sensor and housing. This effect removes carbon from the sensor surface, thus restoring it to its original new condition.

Due to the low operating temperature of the sensor, the temperature is not elevated enough to allow the reaction of $C+O_2 \rightarrow CO_2$ to occur. It has been noted in prior heat treating art, that temperatures above 1200° F. are required for this reaction to occur at an acceptable rate. It is typical that a temperature between 1500° and 1600° F. is required for the reaction to work at a reasonable rate.

The sensor must then be elevated in temperature during the flow of air to allow the reaction to take place. Three different methods are possible for the raising of sensor temperature. The first method would be accomplished by raising the voltage applied to the internal heater. The additional voltage would increase the power and therefore the temperature of the sensor. The problem with this approach is that the heater will fail prematurely or immediately during this procedure. The second method would be accomplished by having a secondary heater that would apply additional heat during the flow of air through the sensor housing. This approach has two potential problems. The first problem exists with the requirement to mount the heater very close to the sensor surface. By doing so, the heater's electrodes must pass through the sensor housing and hermetic sealing of the heater leads would be required. Sealing of the leads would pose a potential leak problem of ambient oxygen during normal operation. Any leaks, even the smallest oxygen leak will cause the sensor to read improperly.

An alternative method for raising the temperature of the sensor for removal of carbon would be to mount the heater outside of the sensor housing. The difficulty with this approach is the extremely long time required to heat the sensor to 1500° F. This could take up to an hour, and also the cool down period could take as long. It is desired to perform the removal of carbon procedure automatically while the sensor is on-line. The external heater approach would cause the sensor to be off-line for several hours which is unacceptable.

The developed method for raising the sensor temperature for the purpose of removing carbon is to allow the internal heater to operate as normal and pass a direct current of electricity through the zirconia/platinum electrolyte. This current flow through the zirconia causes the temperature of the zirconia and, therefore, the sensor to rise. Increasing the current flow will also increase the temperature of the zirconia. This method eliminates the need of a secondary heater and eliminates the fear of premature internal heater failure. Failure of the internal heater makes the sensor worthless and it must be replaced. The adjustable current supply receives its power of the same supply that operates the heater. The supply is adjustable for changes that might occur in sensor manufacture over time. Presently the current flow is set to 40 ma.

The passing of current through the zirconia/platinum interface causes zirconia and the platinum to elevate in temperature on the surface of the sensor. This area is the area where the carbon would have been deposited and, therefore, is ideal for optimizing the removal of carbon. The carbon removal period only is required for five to six minutes. The heating of the zirconia through the passing of current occurs rapidly. This rapid heating allows the carbon reaction to start occurring almost immediately and, therefore, minimizing the time the control system is off-line.

During the time the control system is off-line, the electronic controller for the generator and the valve for adjusting air/fuel ratio are held in a frozen position. This is required because the endothermic gas generator must be held at a steady state condition while the sensor is being removed of carbon and for a short period thereafter.

The passing of current through the sensor's platinum/zirconia interface causes the sensor's temperature to be elevated as described earlier. At a predetermined interval, the microprocessor activates 130a an the air pump 131. This is accomplished by the microprocessor turning on the 135 digital output. Once activated, the air pump begins to run and a three way solenoid valve 133 is deactivated. Deactivating the three way solenoid valve causes the flow of endothermic gas to be inhibited and the flow of air from the pump to begin. With 130a also activated the sensor's output leads 78a, 78b are disconnected from the control microprocessor input leads by opening normally closed contacts 108a, 108b. At the same time, the sensor leads are connected to the current source through normally open contacts 114a, 114b. During this sequence which is set to four minutes and thirty seconds, 130b is still de-energized. With 130b in a de-energized state, current passes through 116a, 116b normally closed contacts. After the four minute thirty second period of time, 136 digital output is activated by the microprocessor and 136 in turn activates 130b. This causes the current flow to reverse through the sensor. Contact 136 remains on for approximately one minute and five seconds.

The reversing of current flow causes the removal of potential carbon to be more complete.

There are applications that do not require the microprocessor instrument for the control of 135, 136 the solenoid valve, the air pump and the control valve motor. For these application, the timing circuit of the control of 135 and 136 is performed by conventional timers. Under these applications, a conventional process controller instrument is also used. The conventional process controller must be connected to an auxiliary contact from contact 135. This auxiliary contact is required to be connected to the instrument's "REMOTE AUTO/MANUAL" contacts. This is required to allow the controller and control valve to be placed in "MANUAL" mode during ht period of time required for carbon removal from the sensor. Most commonly used process controller instruments can be ordered with the "REMOTE AUTO/MANUAL" feature. Control 135 is energized by the timing circuit during the removal of carbon form the sensor. After a four minute thirty second period of time, the timing circuit turns on contact 136 for one minute and five seconds. At the completion of the one minute five second interval, both 135 and 136 are de-energized. At this point in time, the condition timer turns on for fifteen minutes to allow the sensor to stabilize after the burn out period. During the condition time, the solenoid valve is also activated allowing endothermic gas to flow into the sensor instead of air. At the end of the condition period, the "REMOTE AUTO/MANUAL" contact on the controller is released. This allows the controller to now begin controlling the endothermic gas generator again. The timing cycle then repeats every eight or twelve hours.

C. Furnace Application

The invention has been described thus far with reference to an endothermic gas generator environment. In fact, the invention was developed and perfected for the endothermic gas generator arrangement shown and described above since that particular application generated numerous complaints from industrial heat treaters. At the same time, problems have also been encountered with furnace probes, particularly furnace probes used in carburizing furnaces. As previously noted, the operating temperature of a carburizing furnace is necessarily at that temperature, i.e. 1000°-1200° F. at which the furnace atmosphere disassociates to produce elemental carbon which can be infused into the case of the ferrous workpieces being carburized. Thus, furnace oxygen sensing probes are typically exposed to a furnace atmosphere which is depositing carbon as well as gas trace elements of other solids which can likewise interfere with the functioning of the probe. Further, in many furnace applications, internal pressure within the furnace may not be significant and thus furnace oxygen sensor probes are generally developed to be of relatively long length so that a sufficient electrolyte surface is exposed to the furnace atmosphere to sample a truly representative stream of furnace atmosphere. Unfortunately, the long length exposes more of the electrolyte surface to carbon deposition which in turn leads to degradation of the probe of the furnace oxygen sensor probe. In addition, since ambient air must travel along the electrolyte's inner sealed surface, temperature variations at the electrode contacts can and do occur and the accuracy of the furnace probe is adversely affected.

Figure 9:
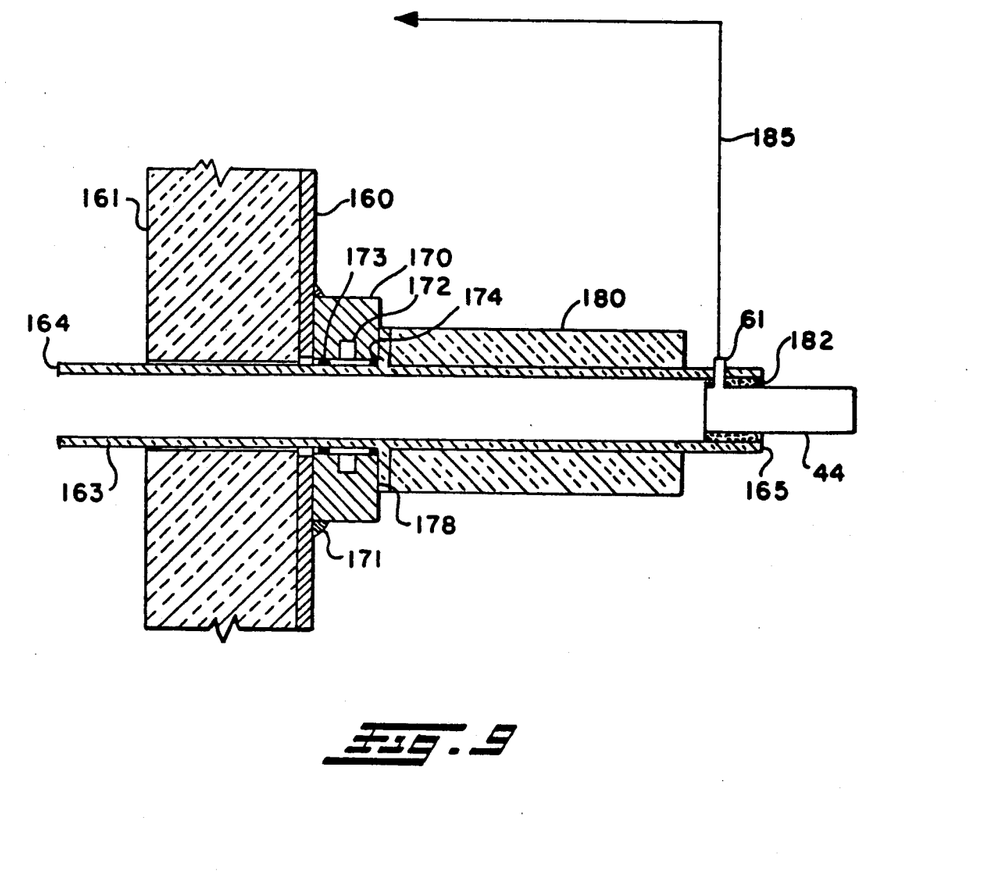
FIG. 9 is a schematic illustration showing the oxygen sensor probe directly applied to the furnace for controlling the sensor probe directly applied to the furnace for controlling the furnace atmosphere therein.

FIG. 9 illustrates an application of the automotive oxygen sensor probe 55 to an industrial heat treating furnace. In FIG. 9, a ceramic tube 163 (silicon carbide) fits into an opening in the furnace casing 160 and furnace insulation 161 so that one of the tube's open end 164 is within the furnace chamber and the other tube's open end 165 is outside the furnace at some predetermined tube length. Ceramic tube 163 can be affixed to furnace casing 160 through any number of conventional different arrangements. In the arrangement shown in FIG. 1, a water jacket block 170 having a central opening close to that of the OD of ceramic tube 163 is secured by weldments 171 to furnace casing 160. Block 170 has a water jacket 172 formed therein and water circulates through jacket 172 in a known manner. An inner and outer elastomer seal 173, 174 engage the outside diameter of ceramic tube 163 to prevent furnace atmosphere from leaking through casing 160. Water jacket 172 keeps o-ring seals 173, 174 cool so that they can effectively seal the tube while also, and importantly, dropping the temperature of the furnace atmosphere within ceramic tube 163 below that temperature at which carbon deposition will occur. Thus, water jacket 172 provides two functions. First, it seals the tube and, second, it prevents the furnace atmosphere from continuing to form carbon when the furnace atmosphere passes to the outside of furnace casing 160. Ceramic tube 163 can be provided with a shoulder 178 which can be secured by fasteners (not shown) to the outside base surface of block 170. If an annular shoulder 178 is used, heat resistance fibrous washers (not shown) would be inserted between shoulder 178 and block 170 to permit thermal expansion between tube and block. Also, optionally, insulation 180 can be wrapped about that portion of tube 163 extending outside furnace casing 160 and, further, water jacket 172 can spiral around the outside diameter of tube 163 so as to control the temperature of the furnace atmosphere in the tube when it reaches sensor housing 44. In fact, the temperature can be controlled so that there is no need to activate internal resistance heater 67.

Sensor housing 44 is mounted to outside end opening 165 of ceramic tube 163 so that the air chamber is exposed to ambient atmosphere and the gas chamber is within tube 163. This can be accomplished by providing a hole in ceramic tube 163 adjacent end 165 and a fitting within exhaust outlet 61 so that the fitting in exhaust outlet 61 snugly fits within the hole in ceramic tube 163. The space between sensor housing 44 and the ID of ceramic tube 163 can be packed with a loose insulation such as Kaowool shown at 182 to prevent furnace atmosphere from passing therethrough. Alternatively, a cap fitting over end 165 can secure sensor housing 44 in its proper relative position. In order to achieve a draw of the furnace atmosphere into ceramic tube 163 which is representative of the furnace atmosphere within the furnace chamber, an air pump (not shown) can be applied to the exhaust conduit 185 connected to exhaust outlet 61 in sensor housing 44. The pump will create a suction causing the furnace atmosphere to travel into the tap inlet of sensor housing 44. However, it is not necessary to use an air pump and, in fact, exhaust conduit 185 can be shaped as a riser vertically extending above sensor housing 44 a sufficient distance and plumbed back through furnace casing 160 into the furnace chamber or vented to atmosphere to act as a manometer creating a sufficient draft to draw the furnace atmosphere into the tap inlet of sensor housing 44.

It should be thus noted that those features of the invention which made the arrangement disclosed herein far superior to the conventional oxygen sensing probe used in the endothermic gas generator application, have been thus retained in the furnace application to provide an economical, long life furnace probe which produces highly accurate consistent readings throughout its life.

In accordance with yet another specific application of the invention, bell-shaped annealing furnaces are typically used in the steel mill art to anneal coiled steel strips stacked on their edges one on top of the other. Reference should be had to assignee's patent, Thekdi 4,310,302, incorporated by reference herein, for a more complete description of such furnaces. Typically, the coiled strip is annealed by injecting an inert gas to purge the furnace and then heating the strip to its annealing temperature for a fixed period of time in the presence of the inert gas. The inert furnace atmosphere, as noted above, is referred to as a neutral atmosphere. In the batch coil annealing application, the inert gas is typically nitrogen (although other inert gases such as argon can be used). The nitrogen gas, commercially supplied the furnace, typically contains 99.98% nitrogen and the balance of 0.02% is oxygen. At elevated temperatures, decarburization occurs. That is, at the annealing temperature, the 0.02% oxygen will draw carbon from the steel. To prevent this from occurring, a scavenger gas, typically hydrogen, is added to the atmosphere. At elevated temperatures, water vapor is formed and decarburization is prevented. Because of the disastrous impact of decarburization on steel strip, conventional practice widely used for batch coil annealers is to provide hydrogen in a 50—50 ratio with nitrogen. Hydrogen is considerably more expensive than nitrogen and significant savings could be affected if the content of the scavenger gas in the furnace atmosphere could be reduced.

The range of the invention's oxygen sensor probe makes it ideal for such application. As noted in FIG. 4, the probe of the present invention generates a millivolt output of about 25 millivolts at stoichiometric conditions which rises to the range of about 1.1 to 1.2 volts when sensing oxygen content on a ppm basis for a rich gas. This characteristic, among other features of the probe, allow it to be used to control the batch coil annealing furnace. Assume, for purposes of discussion, that furnace 30 in FIG. 1 is a batch coil, bell-shaped annealing furnace; that line 26 and valve 35 control the flow of an inert gas into annealing furnace 30 and that a scavenger gas, hydrogen, through a valve (not shown but under control of microprocessor 20) is admitted into annealing furnace 30 at 39. Finally, oxygen sensor housing 44 with its probe is connected to the inner cover or even the base plate of annealing furnace 30 in a manner similar to that shown in FIG. 9 although the cooling jacket is not necessarily required.

Furnace 30 is initially purged by controlling valve 35 with the inert gas (nitrogen) until probe 40 senses a first predetermined electrical signal within an electrical output range typically associated with what the oxygen content in nitrogen would usually be. This would be somewhere in excess of 25 millivolts and significantly less than 1 volt. When this signal is reached, purging is discontinued and a scavenger gas, hydrogen, is admitted at 39 under the control of microprocessor 20 until a second predetermined signal is recorded. This signal is in the range of FIG. 5. The annealing process can then be accomplished with microprocessor controller 20 regulating the flow of hydrogen and nitrogen in accordance with the probe's signal to insure that decarburization does not occur. A significant reduction in furnace atmosphere hydrogen content occurs. Significantly, internal resistance heater 67 allows the proper blending of nitrogen and hydrogen to occur prior to the time when the furnace reaches its operating temperature. That is, the furnace atmosphere composition is established as non-oxidizing prior to heat up. During the heat portion of the annealing cycle, the current inputted to resistance heater 67 can be shut off.

The invention has been described with reference to a preferred embodiment and alternative embodiments thereof. Obviously, modifications and alterations will become apparent to those skilled in the art upon a reading and understanding of the invention described herein. Specifically, the invention can be used outside the industrial furnace area. For example, the sensor housing can be easily modified to fit into the tailpipe of an automobile (not entirely dissimilar to the ceramic tube mounted to the furnace in FIG. 9) and a simplified microprocessor controller 20 supplied with the sensor to measure automotive emissions. The device would work exactly as described above and would afford a low cost, accurate system which could be made available to state testing agencies to insure automotive compliance with federal emissions standards. For commercial applications, automotive emissions testing is far greater than furnace control. However, the invention was developed for furnace control and is disclosed and described with reference thereto. It is intended to include all such modifications and alterations insofar as they come within the scope of the present invention.

Having thus defined the invention, the following is claimed;

1. A method for generating and controlling a neutral furnace atmosphere in an industrial furnace throughout the entire furnace cycle by an oxygen sensing probe having a sensing media with sealed interior and exterior surfaces and contact leads extending from each surface and generating an electrical signal in response to a reference gas flowing over one of said surfaces and furnace gas flowing over the other surface comprising the steps of:
    (a) purging said furnace with an inert gas until a first predetermined electrical signal indicative of a lean, substoichiometric, furnace atmosphere having a predetermined oxygen content is generated from said sensor;
    (b) thereafter admitting a scavenger gas of a generally reducing nature into said furnace until a second predetermined electrical signal indicative of a furnace atmosphere varying from stoichiometric to reducing is generated form said sensor; and
    (c) thereafter independently controlling the composition and rate of flow of said inert gas and said scavenger gas admitted to said furnace when said furnace is heated to its operating temperature in accordance with said second predetermined signal to minimize consumption of said scavenger gas.

2. The method of claim 1 wherein said furnace is a bell-shaped, batch coil annealing furnace and said inert gas is nitrogen containing about two per cent oxygen and said scavenger gas is hydrogen.

* * * * *